(12) United States Patent
Liu et al.

(10) Patent No.: US 11,622,874 B2
(45) Date of Patent: Apr. 11, 2023

(54) GUIDE CAP AND LOADING SYSTEM FOR LOADING IMPLANT INTO DELIVERY SYSTEM

(71) Applicant: Shanghai Microport Cardioflow Medtech Co., Ltd., Shanghai (CN)

(72) Inventors: Xiang Liu, Shanghai (CN); Mingming Wu, Shanghai (CN); Baozhu Gui, Shanghai (CN); Guoming Chen, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 1248 days.

(21) Appl. No.: 16/127,895

(22) Filed: Sep. 11, 2018

(65) Prior Publication Data

US 2018/0369004 A1   Dec. 27, 2018

Related U.S. Application Data

(63) Continuation of application No. 15/032,456, filed as application No. PCT/CN2014/089979 on Oct. 31, 2014, now Pat. No. 10,098,769.

(30) Foreign Application Priority Data

Oct. 31, 2013   (CN) .......................... 201310534075.3

(51) Int. Cl.
*A61F 2/95*   (2013.01)
*A61F 2/24*   (2006.01)
(Continued)

(52) U.S. Cl.
CPC .............. *A61F 2/95* (2013.01); *A61F 2/2418* (2013.01); *A61F 2/2436* (2013.01);
(Continued)

(58) Field of Classification Search
CPC ..... A61F 2/9525; A61F 2/2427; A61F 2/9522
See application file for complete search history.

(56) References Cited

U.S. PATENT DOCUMENTS 5,725,519 A      3/1998   Penner et al.
10,098,769 B2 *  10/2018  Liu ........................ A61F 2/2418
(Continued)

FOREIGN PATENT DOCUMENTS

CN      101460115 A    6/2009
CN      101897629 A    12/2010
(Continued)

*Primary Examiner* — Alexander J Orkin
(74) *Attorney, Agent, or Firm* — Muncy, Geissler, Olds & Lowe, P.C.

(57) ABSTRACT

A guide cap and a loading system for loading an implant into a delivery system are disclosed which are capable of simplifying operations required in interventional surgery using the implant. The guide cap has a lumen passing therethrough and includes: a conical section; a straight or conical tube in communication with a small open end of the conical section; and a flange, wherein a large open end of the conical section flares outward and thereby forms the flange. The loading system includes a guider and the guide cap. During the process of loading the implant into the delivery system, the guide cap enables the valve prosthesis to be coupled to the connector of the delivery system and allows the valve prosthesis to be compressed so as to be entirely capsuled in the delivery system with relatively easy and quick operations, thereby reducing surgery time during its clinical use.

7 Claims, 7 Drawing Sheets

(51) Int. Cl.
*A61F 2/962* (2013.01)
*B65B 5/04* (2006.01)

(52) U.S. Cl.
CPC ............ *A61F 2/9525* (2020.05); *A61F 2/962* (2013.01); *B65B 5/04* (2013.01); *A61F 2/9522* (2020.05); *A61F 2002/9528* (2013.01); *Y10T 29/53909* (2015.01); *Y10T 29/53917* (2015.01); *Y10T 29/53987* (2015.01)

(56) References Cited

U.S. PATENT DOCUMENTS

| | | | |
|---|---|---|---|
| 2002/0183827 A1* | 12/2002 | Derus | A61L 31/06 623/1.12 |
| 2007/0162100 A1 | 7/2007 | Gabbay | |
| 2007/0239271 A1 | 10/2007 | Nguyen | |
| 2009/0192601 A1* | 7/2009 | Rafiee | A61F 2/2436 623/2.11 |
| 2010/0043197 A1 | 2/2010 | Abbate et al. | |
| 2010/0292780 A1 | 11/2010 | Straubinger et al. | |
| 2010/0298931 A1 | 11/2010 | Quadri et al. | |
| 2012/0083875 A1 | 4/2012 | Johnson et al. | |
| 2012/0226341 A1 | 9/2012 | Schreck et al. | |
| 2012/0330408 A1 | 12/2012 | Hillukka et al. | |
| 2013/0030418 A1* | 1/2013 | Taft | A61F 2/9525 606/1 |
| 2013/0116772 A1* | 5/2013 | Robinson | A61F 2/966 623/1.12 |
| 2013/0190859 A1* | 7/2013 | Hillukka | A61F 2/2418 623/2.11 |
| 2014/0331475 A1 | 11/2014 | Duffy et al. | |

FOREIGN PATENT DOCUMENTS

| | | |
|---|---|---|
| CN | 102144940 A | 8/2011 |
| CN | 103096838 A | 5/2013 |
| CN | 103179919 A | 6/2013 |
| CN | 103349577 A | 10/2013 |
| JP | 2009533139 A | 9/2009 |
| WO | WO 2007/120543 A1 | 10/2007 |
| WO | WO 2012/023979 A2 | 2/2012 |
| WO | WO 2012/106491 A1 | 8/2012 |

* cited by examiner

GUIDE CAP AND LOADING SYSTEM FOR LOADING IMPLANT INTO DELIVERY SYSTEM

CROSS-REFERENCE TO RELATED APPLICATIONS

This application is a Continuation of co-pending application Ser. No. 15/032,456 filed on Apr. 27, 2016 for which priority is claimed under 35 U.S.C. § 120; and this application claims priority of PCT Application No. PCT/CN2014/089979 filed on Oct. 31, 2014; and claims priority of Application No. 201310534075.3 filed in CHINA on Oct. 31, 2013 under 35 U.S.C. § 119, the entire contents of all of which are hereby incorporated by reference.

TECHNICAL FIELD

The present invention relates to a guide cap and a loading system for loading an implant into a delivery system.

BACKGROUND

Heart valve diseases are some of the most commonly diagnosed cardiac diseases in China, and some of them are found to be heart valve damage caused by rheumatic fever. In recent years, the continually aging population has driven an increasing incidence of valvular degeneration (including calcification, mucoid degeneration, etc.) and valvular damage caused by metabolic disorders in China.

Minimally invasive interventional surgery offers a variety of advantages, including needlessness of sternotomy, minimal patient trauma and quick recovery. In the recent ten years, the development shows that not only the diseases curable by traditional medical and surgical treatments but also some diseases that the traditional approaches could not handle can be treated by the interventional therapies. After entering the twenty-first century, researches on interventional therapies for valvular heart diseases have been experiencing a notable acceleration. Percutaneous valve implant techniques have evolved from experimental researches to small-scale clinical trials and are likely to have breakthroughs in technical "bottlenecks" to achieve extensive clinical applications. This makes the techniques again a focus of research efforts in the field of interventional cardiology.

CN101460115A describes a device for loading an interventional heart valve into a delivery system. The device is composed of an inflow cone 42, an inflow tube 38, an outflow cone 34, an outflow tube 40 and a cap 36. The interventional heart valve is crimped and introduced into the outflow cone 34 with the aid of the cap 36 such that one end of the interventional valve is compressed by the outflow cone 34. The inflow tube 38 is then inserted through an aperture of the cap 36 such that the compressed portion of the interventional valve is expanded to a size that is comparable to a size of a catheter of the delivery system, thereby allowing a stent of the interventional valve to be coupled to the delivery system. The delivery system is then manipulated to cause a sheath of the catheter and the outflow tube to move so as to allow the interventional valve stent to be partially loaded within the delivery system. Subsequently, the cap and the outflow cone are retrieved, and the other end of the interventional valve stent is compressed into the inflow cone. The remaining portion of the interventional valve stent is then reduced in size, and the delivery system is manipulated to receive the whole of the interventional valve stent. This device, however, requires complicated operations during its use in surgery.

SUMMARY OF THE INVENTION

It is therefore an objective of the present invention to provide guide a cap and a loading system for loading an implant into a delivery system, which can simplify operations required in interventional surgery using the implant. Other advantages of the present invention will be described below with reference to specific embodiments.

To this end, according to one aspect, the present invention provides a guide cap for loading an implant into a delivery system.

The guide cap for loading an implant into a delivery system of the present invention has a lumen passing therethrough and includes: a conical section; a straight or conical tube in communication with a small open end of the conical section; and a flange, wherein a large open end of the conical section flares outward and thereby forms the flange.

Optionally, the lumen may include a first lumen and a second lumen, the first lumen being inside the conical section, the second lumen being inside the straight or conical tube, the first lumen having a conical shape, the second lumen having a cylindrical or conical shape.

Optionally, the second lumen may have a conical shape and has a conical degree smaller than a conical degree of the first lumen.

Optionally, the flange may define an annular groove.

Optionally, a transition section may be provided between the conical section and the straight or conical tube.

Optionally, the implant may be a heart valve stent.

According to another aspect, the present invention also provides a loading system for loading an implant into a delivery system.

The loading system for loading an implant into a delivery system of the present invention includes a guider and a guide cap, wherein the guide cap having a lumen passing therethrough and including: a conical section; a straight or conical tube in communication with a small open end of the conical section; and a flange, wherein a large open end of the conical section flares outward and thereby forms the flange, wherein the guider has a circumferential surface tapered along an axis of the guider and thus forms a large open end at a first edge and a small open end at a second edge of the circumferential surface, the small open end of the guider having a diameter greater than a diameter of the small open end of the conical section of the guide cap; and wherein the guide cap and the guider are so sized that the flange is able to cover the large open end of the guider, with an end portion of the straight or conical tube protruding from the small open end of the guider.

Optionally, the flange may define notches; the guider has tabs at the first edge corresponding to the large open end; and the tabs pass through the notches when the guide cap covers the guider.

Optionally, the guider may have two tapered inner surfaces and have a large open end and a small open end at edges of the two tapered inner surfaces; a large open end of a first one of the two tapered inner surfaces provides the large open end of the guider; a small open end of the first one of the two tapered inner surfaces has a diameter equal to or slightly smaller than a diameter of a large open end of a second one of the two tapered inner surfaces, and is coupled to the large open end of the second one of the two tapered inner surfaces; and the small open end of the second one of the two tapered inner surfaces provides the small open end of the guider.

According to the present invention, during the process of loading the implant into the delivery system, the guide cap enables the valve prosthesis to be coupled to the connector of the delivery system and allows the valve prosthesis to be compressed so as to be entirely capsuled in the delivery system with relatively easy and quick operations, thereby reducing surgery time during its clinical use.

BRIEF DESCRIPTION OF THE DRAWINGS

The present invention will be better understood with reference to the accompanying drawings provided without limiting the invention, in which.

DETAILED DESCRIPTION

Exemplary embodiments of the present invention will be described below with reference to the accompanying drawings. While various details of embodiments of the present invention are set forth in the following detailed description to facilitate understanding, they are to be construed as illustrative only. Accordingly, it is to be appreciated by those of ordinary skill in the art that the embodiments disclosed herein are susceptible to various alterations and modifications without departing from the scope and sprit of the present invention. Further, for the sake of clarity and conciseness, description of some well-known functions and structures is omitted.

In one embodiment, the device for loading an implant into a delivery system, according to the present invention, includes a guide cap, a guider and a guiding tube, which are described below in greater detail with reference to the accompanying drawings.

Figure 1A:
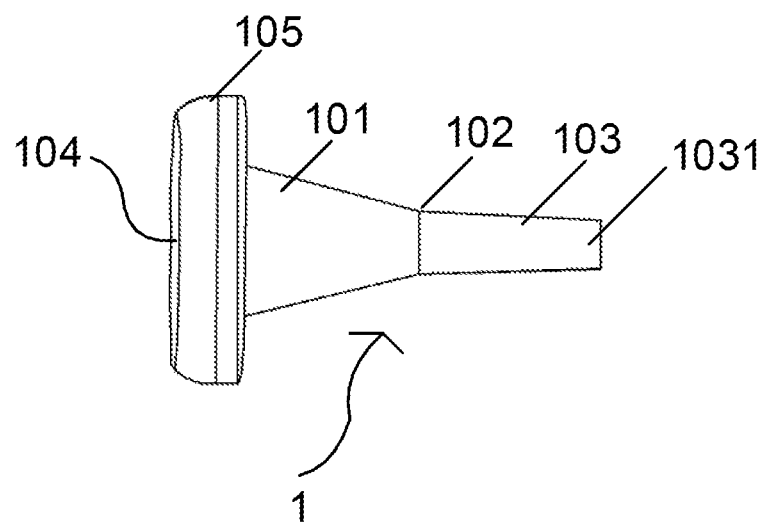
FIGS. 1A, 1B and 1C schematically illustrate a guide cap in accordance with one embodiment of the present invention.
Figure 1B:
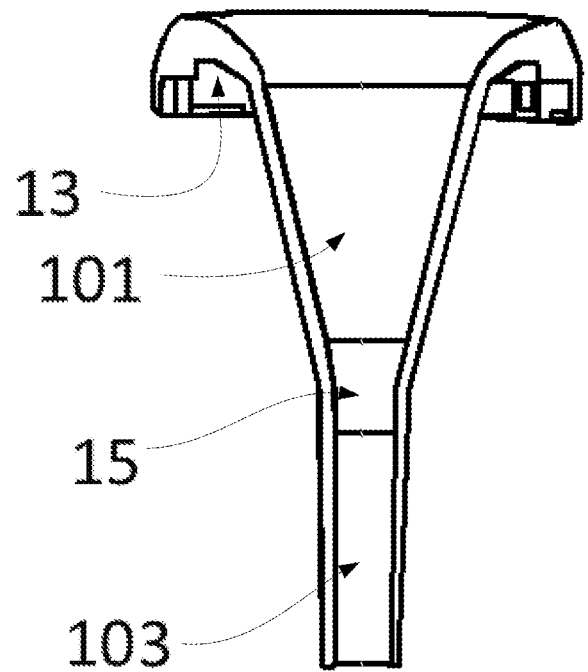
Figure 1C:
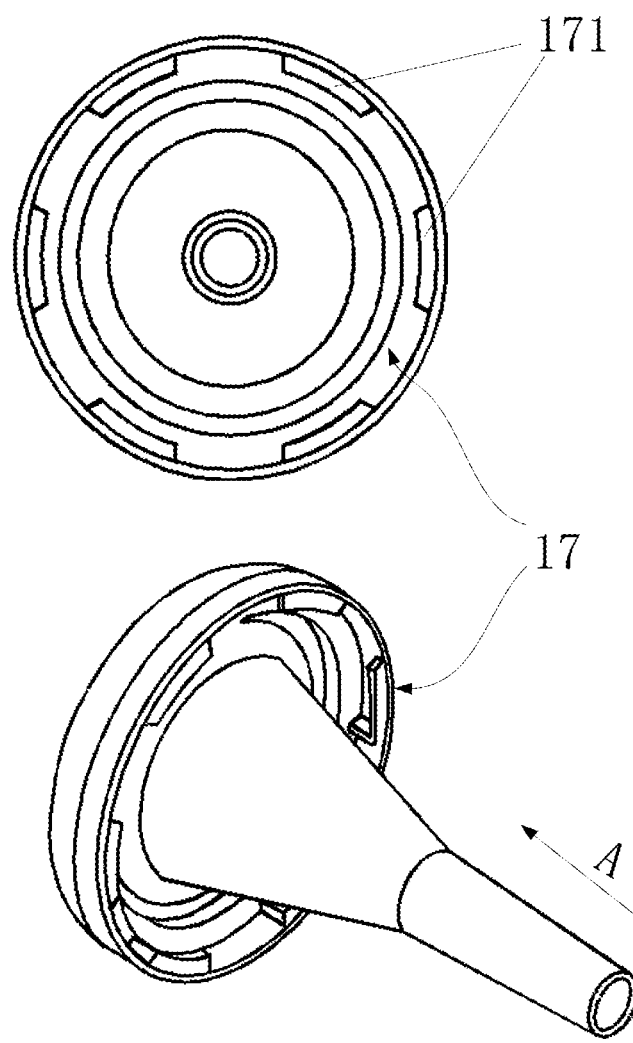

FIGS. 1A, 1B and 1C are schematic illustrations of a guide cap in accordance with one embodiment of the present invention, in which, FIG. 1A shows a profile of the guide cap, FIG. 1B is a cross section taken along an axis of the guide cap, and FIG. 1C includes a perspective view of the guide cap and a diagram showing the guide cap when viewed along the direction A. As shown in FIGS. 1A and 1B, the guide cap 1 has a conical section 101 and a straight or conical tube 103 which communicates with a small open end 102 of the conical section. A large open end 104 of the conical section flares outward, thereby forming a flange 105 facing the straight or conical tube 103. The flange 105 may define an annular groove 13. In the guide cap 1, a curved transition section 15 may connect the conical section 101 to the straight or conical tube 103, such that the guide cap 1 has a smooth interior surface to facilitate movement of the implant within the guide cap.

The guider has a circumferential wall, which is a circumferential wall that is tapered along an axis of the guider, thereby forming a large opening at one end and a small opening at the other end. The small opening has a diameter that is greater than a diameter of a free end 1031 of the straight or conical tube 103. In addition, the guide cap and the guider are so sized that the large open end of the guider can be covered by and fixed to the flange 105, with the free end 1031 passing through the guider and protruding from the smaller opening of the guider.

Figure 2A:
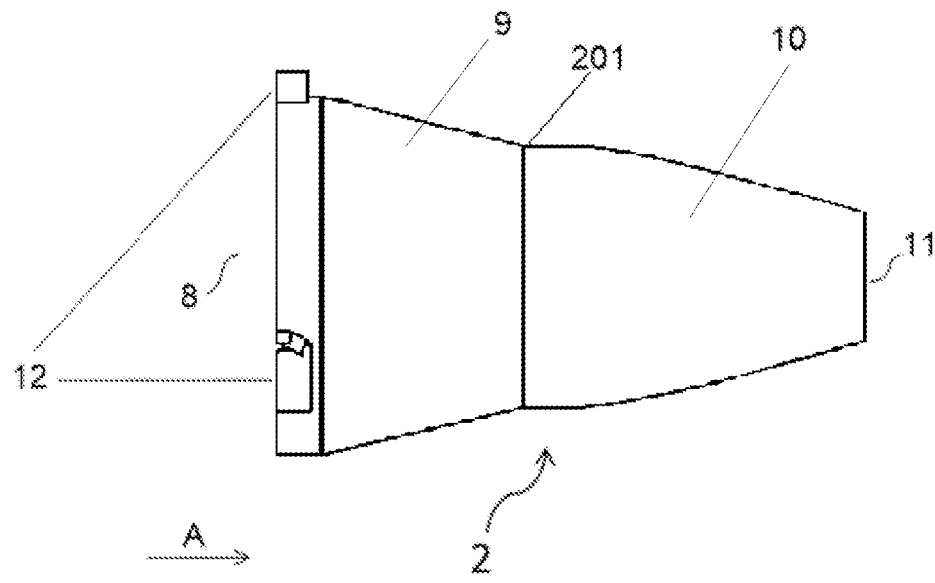
FIGS. 2A and 2B schematically illustrate a preferred embodiment of a guider in accordance with one embodiment of the present invention.
Figure 2B:
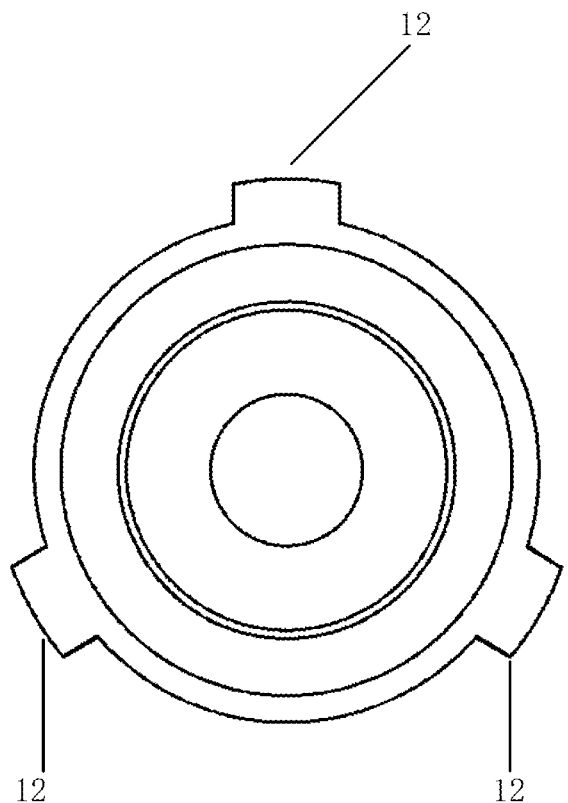

The guider can be generally a portion of a cone. However, in a preferred embodiment as shown in FIGS. 2A and 2B, the guider consists of two tapered section joined to each other. FIGS. 2A and 2B schematically illustrate a preferred embodiment of a guider in accordance with one embodiment of the present invention, in which FIG. 2B shows the guider of FIG. 2A when viewed along the A direction. As illustrated in FIGS. 2A and 2B, the guider 2 has a first tapered section 9 and a second tapered section 10 which are joined together and respectively provide the large open end 8 and the small open end 11, of the guider. At the interface 201 of the tapered sections 9 and 10, the first tapered section 9 has a diameter slightly larger than a diameter of the second tapered section 10. That is to say, the guider 2 slightly shrinks in size at its middle portion. This prevents the implant from automatically escaping from the guider and facilitates the prosthesis implantation procedure.

The flange 105 of the guide cap is coupled to the large open end of the guider 2 by means of either a frictional force or the combination of notches 17 of FIG. 1C and tabs 12 of FIG. 2B. The notches 17 are arranged in the flange 105 and defined by several protrusions 171 protruding radially towards the conical section 101 from the edge of the flange 105 (FIG. 1C). There are a plurality of tabs 12 arranged in a plane defined by the edge of the large open end 8 of the guider 2. As such, when the flange 105 covers the large open end 8 of the guider 2 with the tabs 12 having passed through the respective notches 17, properly rotating the flange 105 can make the tabs 12 blocked by the respective protrusions 171, thereby locking the flange 105 and the guider 2 together.

Figure 3A:
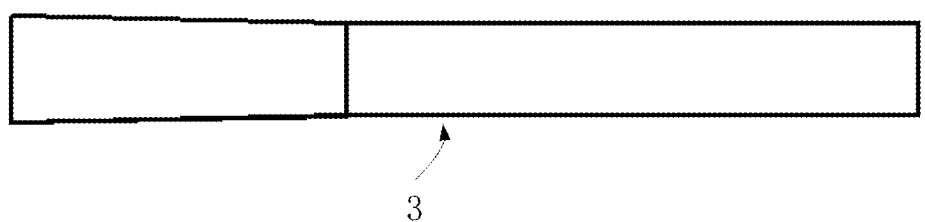
FIGS. 3A and 3B are schematics illustrating a guiding tube in accordance with one embodiment of the present invention.
Figure 3B:
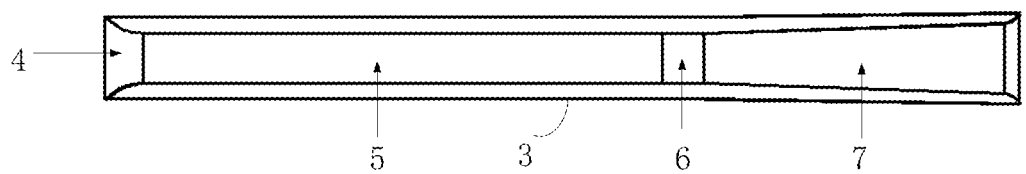

FIGS. 3A and 3B schematically illustrate a guiding tube in accordance with an embodiment of the present invention. FIG. 3A shows the outer appearance of the guiding tube, while FIG. 3B shows a cross section of the guiding tube. As shown in FIG. 3B, the guiding tube 3 includes a straight tubular section 5 and a conical tubular section 7. Optionally, a curved transition section 6 may also be provided between the sections 5 and 7 to ensure a smooth inner surface of the guiding tube 3. Alternatively, the guiding tube 3 may also be composed of one or two conical tubular sections. In either case, the conical tubular section(s) is/are required to have a much smaller conical angle. The open end of the conical tubular section 7 has a diameter between a diameter of the small open end 102 of the conical section 101 of the guide cap 1 and a diameter of the small open end 11 of the guider 2. The straight tubular section 5 may have an internal chamfer or fillet 4 at the free end for facilitating the assembly with a catheter.

With the foregoing device according to embodiments of the present invention, an implant can be loaded into a delivery system by following the steps as shown in FIGS. 4 to 12. A description is set forth below to explain how the device operates with reference to FIGS. 4 to 12.

Figure 4:
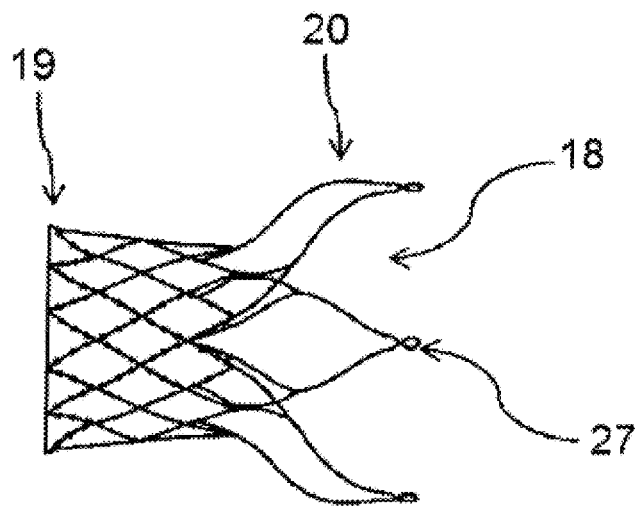
FIG. 4 shows a valve prosthesis applicable to the embodiments of the present invention.

The device according to the present invention may be used to load an implant such as a heart valve prosthesis into a delivery system such as a catheter. FIG. 4 shows such a valve prosthesis applicable to the embodiments of the present invention. As illustrated in FIG. 4, the valve prosthesis 18 has a valve inflow end 19 and a valve outflow end 20 provided with valve ears 27.

Figure 5:
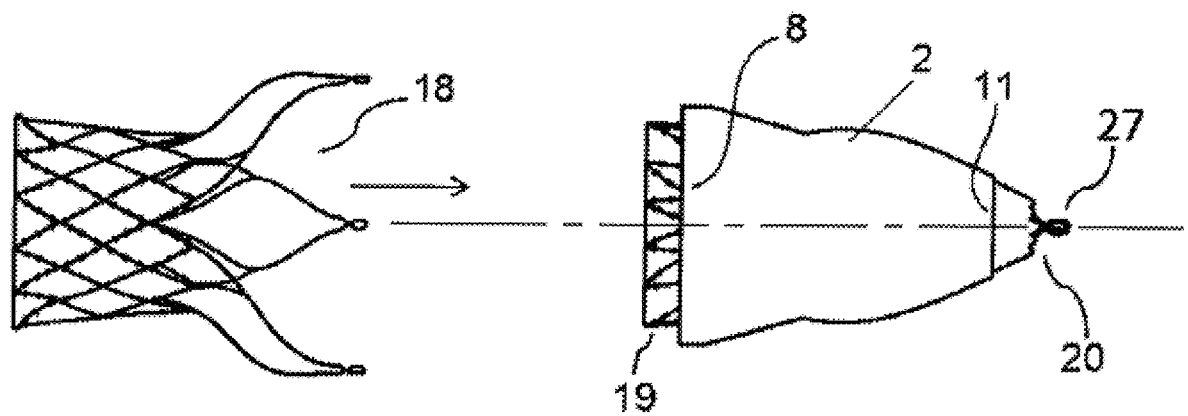
FIG. 5 shows the implant being received in the guider in accordance with one embodiment of the present invention.

FIG. 5 shows the implant being placed in a guider in accordance with one embodiment of the present invention. As shown in the FIG. 5, the valve prosthesis 18 is first loaded into the guider 2 (along the direction as indicated by the arrow in the figure) in such a manner that the valve outflow end 20 of the valve prosthesis 18 is introduced into the guider 2 from the large open end 8 of the guider 2 and protrudes from the small open end 11, with the valve inflow end 19 being also exposed outside the large open end 8 of the guider 2.

Figure 6A:
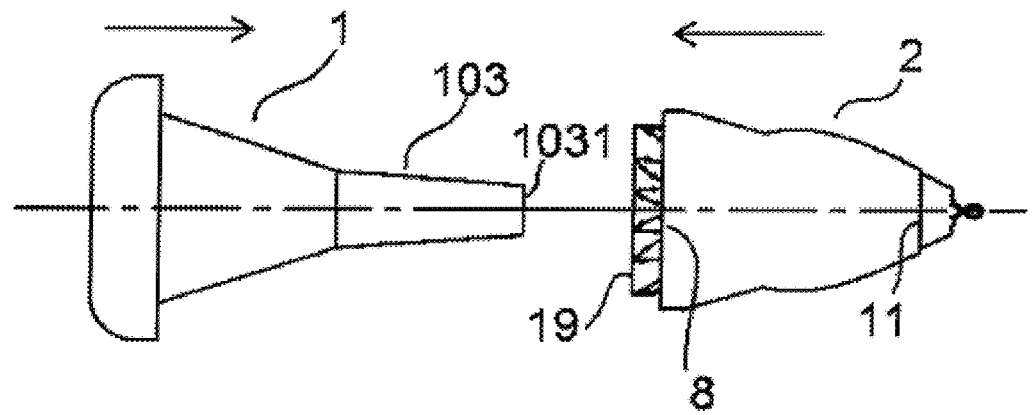
FIGS. 6A and 6B shows interlocking of the guide cap and the guider in accordance with one embodiment of the present invention.
Figure 6B:
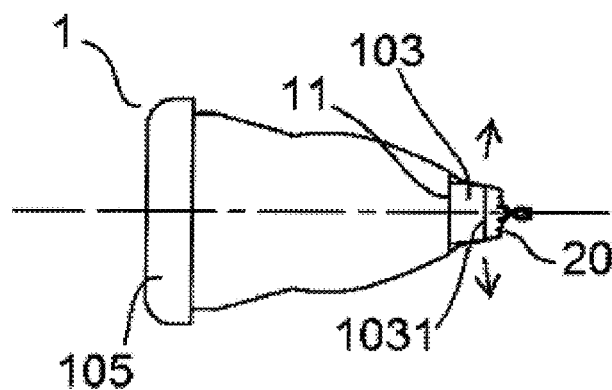

FIGS. 6A and 6B schematically illustrate the interlocking of guide cap and guider in accordance with one embodiment of the present invention. As shown in FIG. 6A, the guide cap 1 and the guider 2 are first moved toward each other in the opposite directions indicated by the arrows, such that the straight or conical tube 103 of the guide cap 1 enters the guider 2 from the large open end 8 and extends within the valve prosthesis 18 in the guider 2. Subsequently, as shown in FIG. 6B, the free end 1031 of the straight or conical tube 103 of the guide cap 1 protrudes from the small open end 11 of the guider 2, thereby expanding the outflow end 20 of the valve prosthesis (as indicated by the arrow in FIG. 6B). In this case, the inflow end 19 is received within the groove 13 (not shown in the figure) defined by the flange 105 of the guide cap 1 and the inflow end 19 is thus prevented from being undesirably deformed by any force.

Figure 7:
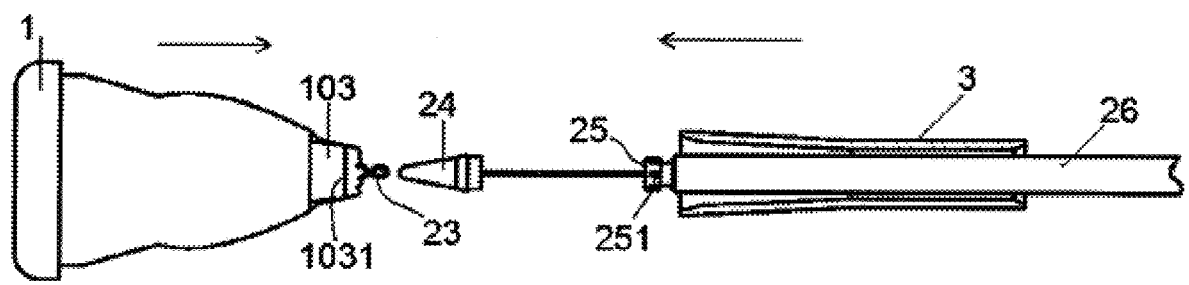
FIG. 7 shows locking of the valve prosthesis to a delivery system in accordance with an embodiment of the present invention.
Figure 8:
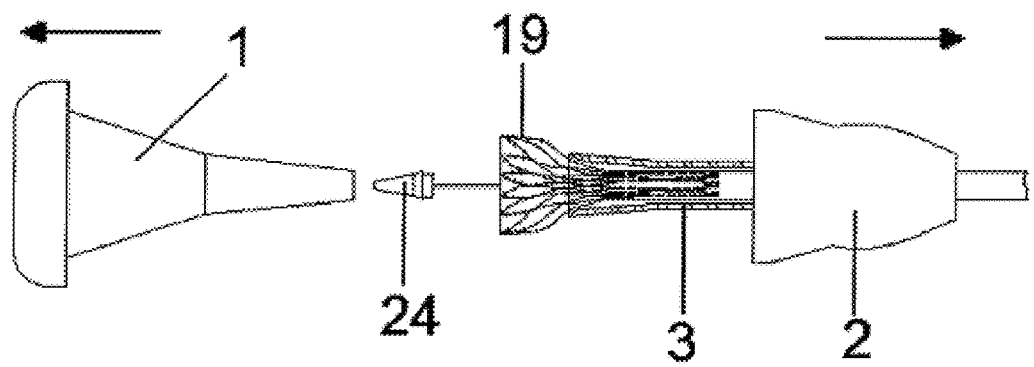
FIG. 8 shows unlocking of the guide cap from the guider in accordance with an embodiment of the present invention.

FIG. 7 schematically illustrates coupling of the valve prosthesis to a delivery system, in accordance with an embodiment of the present invention. As shown in FIG. 7, the guiding tube 3 is first disposed over a catheter 26 of the delivery system. The delivery system and the guider 2 carrying the valve prosthesis 18 are then moved in opposite directions toward each other (as indicated by the arrows in the figure). In this process, a guide tip 24 of the delivery system enters the guide cap 1 from the free end 1031 of the straight or conical tube 103 of the guide cap 1 to allow the ears 23 to be engaged with hooks 251 (with reference to FIG. 8) projecting from the surface of a connector 25 of the delivery system. The guiding tube 3 is then moved to partially compress the prosthesis, and the catheter 26 of the delivery system is also moved such that the prosthesis is partially loaded in the catheter. After that, the guiding tube 3 is further moved to accommodate an additional portion of the implant, and this process may be repeated until not any more portion of the implant could be further accommodated in the guiding tube and loaded in the catheter due to a strong radial force, as shown in FIG. 8. In addition, since the diameter of the conical tubular section 7 at the open end is between the diameter of the straight or conical tube 103 at the free end 1031 and the diameter of the guider 2 at the small open end 11, in the configuration of FIG. 7, the movement of the guiding tube 3 will cause itself to partially enter the guider 2 from the small open end 11 so that a portion of the implant is received in the guiding tube and is hence reduced in radial size. This facilitates subsequent movement of the guider 2 toward the right side, as shown in FIG. 8, which is a schematic illustrating unlocking of the guide cap from the guider, in accordance with an embodiment of the present invention. As illustrated in FIG. 8, the guide cap 1 and guider 2 are unlocked from each other and moved in opposite directions away from each other (as indicated by the two arrows in the figure).

Figure 9:
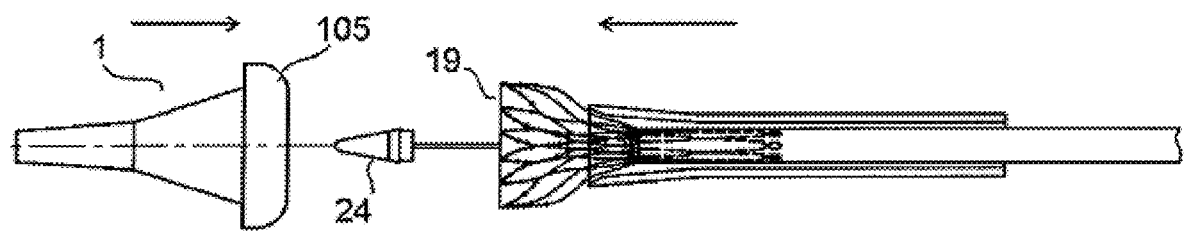
FIG. 9 shows further compressing of the valve prosthesis due to the guide cap in accordance with one embodiment of the present invention.
Figure 10:
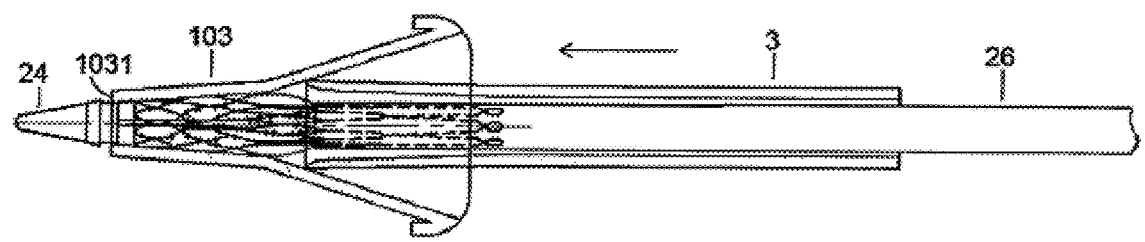
FIG. 10 shows the valve prosthesis being loaded in the guide cap in accordance with one embodiment of the present invention.

FIG. 9 shows further compressing of the valve prosthesis due to the guide cap 1 in accordance with one embodiment of the present invention. As shown in FIG. 9, the guide cap 1 is oriented with the flange 105 facing the guide tip 24 of the delivery system. In this state, moving the guide cap and the delivery system in opposite directions toward each other (as indicated by the arrows in the figure) can lead to further compressing of the valve inflow end 19 as well as a proximal portion thereof. As a result, as shown in FIG. 10, the guide tip 24 of the delivery system protrudes from the free end 1031 of the straight or conical tube 103 of the guide cap. FIG. 10 shows the valve prosthesis being received in the guide cap in accordance with one embodiment of the present invention.

Figure 11:
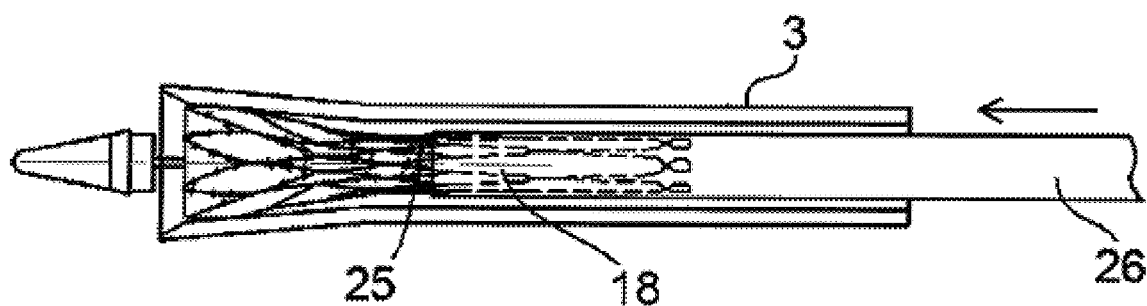
FIG. 11 shows the valve prosthesis being received in the guiding tube, in accordance with an embodiment of the present invention.

In the configuration of FIG. 10, when the guiding tube 3 is moved along the direction indicated by the arrow, concurrently with the catheter 26 of the delivery system being maintained stationary, the guide cap 1 will be pushed off by the guiding tube 3, with the valve prosthesis 18 being accommodated in the guiding tube 3, as shown in FIG. 11, which is a schematic depicting the valve prosthesis being received in the guiding tube 3, in accordance with an embodiment of the present invention.

Figure 12:
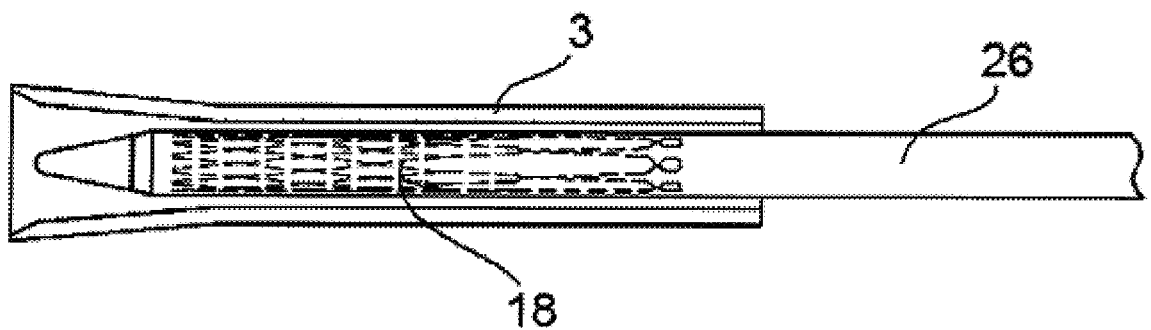
FIG. 12 shows the valve prosthesis being wholly loaded in the delivery system in accordance with an embodiment of the present invention.

As shown in FIG. 11, when the catheter 26 of the delivery system is advanced in the direction indicated by the arrow to make both the connector 25 of the delivery system and the valve prosthesis located between the connector 25 and the guide tip 24 of the delivery system to enter into the catheter 26 of the delivery system. Then the valve prosthesis 18 will be entirely loaded in the delivery system, as shown in FIG. 12, which is a schematic illustrating the valve prosthesis being wholly loaded in the delivery system, in accordance with an embodiment of the present invention. In the configuration of FIG. 11 or 12, the guider 2 can be removed from the open end of the conical tubular section 7 of the guiding tube 3.

As apparent from the foregoing description of the process to load the prosthesis into the delivery system, the guide cap enables the valve prosthesis to be coupled to the connector of the delivery system and allows the valve prosthesis to be compressed to be entirely received in the delivery system with relatively easy and quick operations, thereby reducing surgery time during its clinical use. In view of the structure of the device according to the above embodiments, the loading of the prosthetic valve can be accomplished with only three components which are distinct in appearance without causing confusions. The slight shrinkage in radial dimension of the guider at the middle portion enables the valve prosthesis to be received therein without escaping and causing interruptions. The guiding tube having a relatively long tapered tubular portion or being implemented completely as a tapered tube provides protection to the catheter of the delivery system, and allows a larger tubular opening which is adapted to loading more types of valve prostheses in various shapes more easily without causing damage to them. All of these advantages are helpful in smooth operations during the clinical use of the device in surgery.

The specific embodiments presented above do not limit the scope of the present invention in any way. Those skilled in the art will appreciate that various modifications, combinations, sub-combinations and substitutions are still possible depending on design requirements and other considerations. It is intended that all variations, equivalent substitutions and modifications made within the spirit and principles of the present invention fall within the scope thereof.

What is claimed is:

1. A loading system for loading an implant into a delivery system, comprising a guider and a guide cap, wherein the guide cap having a lumen passing therethrough and comprising:
    a conical section;
    a straight or conical tube in communication with a small open end of the conical section; and
    a flange, wherein a large open end of the conical section flares outward and thereby forms the flange,
    wherein the guider has a circumferential surface tapered along an axis of the guider and thus forms a large open end at a first edge and a small open end at a second edge of the circumferential surface, the small open end of the guider having a diameter greater than a diameter of the small open end of the conical section of the guide cap; and
    wherein the guide cap and the guider are so sized that the flange is able to cover the large open end of the guider, with an end portion of the straight or conical tube protruding from the small open end of the guider,
    wherein the lumen comprises a first lumen and a second lumen, the first lumen being inside the conical section, the second lumen being inside the straight or conical tube, the first lumen having a conical shape, the second lumen having a cylindrical or conical shape.

2. The loading system according to claim 1, wherein:
    the flange defines notches;
    the guider has tabs at the first edge corresponding to the large open end; and
    the tabs pass through the notches when the guide cap covers the guider.

3. The loading system according to claim 1, wherein:
    the guider has two tapered inner surfaces and has a large open end and a small open end at edges of the two tapered inner surfaces;
    a large open end of a first one of the two tapered inner surfaces provides the large open end of the guider;
    a small open end of the first one of the two tapered inner surfaces has a diameter equal to or slightly smaller than a diameter of a large open end of a second one of the two tapered inner surfaces, and is coupled to the large open end of the second one of the two tapered inner surfaces; and
    the small open end of the second one of the two tapered inner surfaces provides the small open end of the guider.

4. The loading system according to claim 1, wherein the second lumen has a conical shape and has a conical degree smaller than a conical degree of the first lumen.

5. The loading system according to claim 1, wherein the flange defines an annular groove.

6. The loading system according to claim 1, wherein a transition section is provided between the conical section and the straight or conical tube.

7. The loading system according to claim 1, wherein the implant is a heart valve stent.

* * * * *